(12) United States Patent
Le Van Mao

(10) Patent No.: US 7,135,602 B1
(45) Date of Patent: Nov. 14, 2006

(54) METHOD AND APPARATUS FOR SELECTIVE DEEP CATALYTIC CRACKING OF HYDROCARBONS

(75) Inventor: Raymond Le Van Mao, Saint-Laurent (CA)

(73) Assignee: Valorbec Societe en Commandite, Montreal (CA)

( * ) Notice: Subject to any disclaimer, the term of this patent is extended or adjusted under 35 U.S.C. 154(b) by 622 days.

(21) Appl. No.: 10/129,577

(22) PCT Filed: Nov. 3, 2000

(86) PCT No.: PCT/CA00/01327

§ 371 (c)(1),
(2), (4) Date: Sep. 4, 2002

(87) PCT Pub. No.: WO01/32806

PCT Pub. Date: May 10, 2001

Related U.S. Application Data

(60) Provisional application No. 60/163,459, filed on Nov. 4, 1999.

(51) Int. Cl.
C07C 4/02 (2006.01)
(52) U.S. Cl. .................. 585/324; 585/650; 585/652; 585/653
(58) Field of Classification Search ............. 585/324, 585/650, 652, 653
See application file for complete search history.

(56) References Cited

U.S. PATENT DOCUMENTS 2,692,193 A 10/1954 Riesz et al.
4,732,881 A 3/1988 Le Van Mao

FOREIGN PATENT DOCUMENTS

EP 0 022 883 1/1981

OTHER PUBLICATIONS

Vasil'EVA et al. "The catalytic pyrolysis of hydrocarbons." *Kinetics and Catalysts*, vol. 21, No. 1, pp. 175-179, 1980.

Primary Examiner—Thuan D Dang
(74) Attorney, Agent, or Firm—Merchant & Gould P.C.

(57) ABSTRACT

Provided herein is a method and apparatus for selective deep catalytic cracking of petroleum naphthas or other hydrocarbon feedstocks. The feed comprising the hydrocarbons to be cracked and steam, in well-defined proportions, is first sent into a precatalytic zone (Zone I) of a cracking reactor, preferably a tubular reactor. In a preferred embodiment, Zone I, contains beads of some catalytically mildly active porous material such as quartz or quartz doped with Cr—Al, is set at a temperature $T_1$. The gas steam flows then through a catalyst bed, called Zone II, where the catalytic reaction takes place. Zone II is set at temperature $T_2$ and contains a zeolite type catalyst, preferably ZSM5 zeolite or, most preferably, a hybrid zeolite catalyst. It is shown that by moderately increasing the temperature $T_1$ of Zone I, it is possible to have an increased total conversion of n-hexane used as model molecule for petroleum naphthas and an increased yield of light olefins (and aromatics), when compared to the parent ZSM-5 zeolite catalyst The ethylene/propylene product ratio is closely dependent of the temperature $T_1$, if all other reaction parameters are kept constant and can be widely varied (from 1.0 to 2.0 for instance) for a limited range of variation of temperature $T_1$.

10 Claims, 2 Drawing Sheets

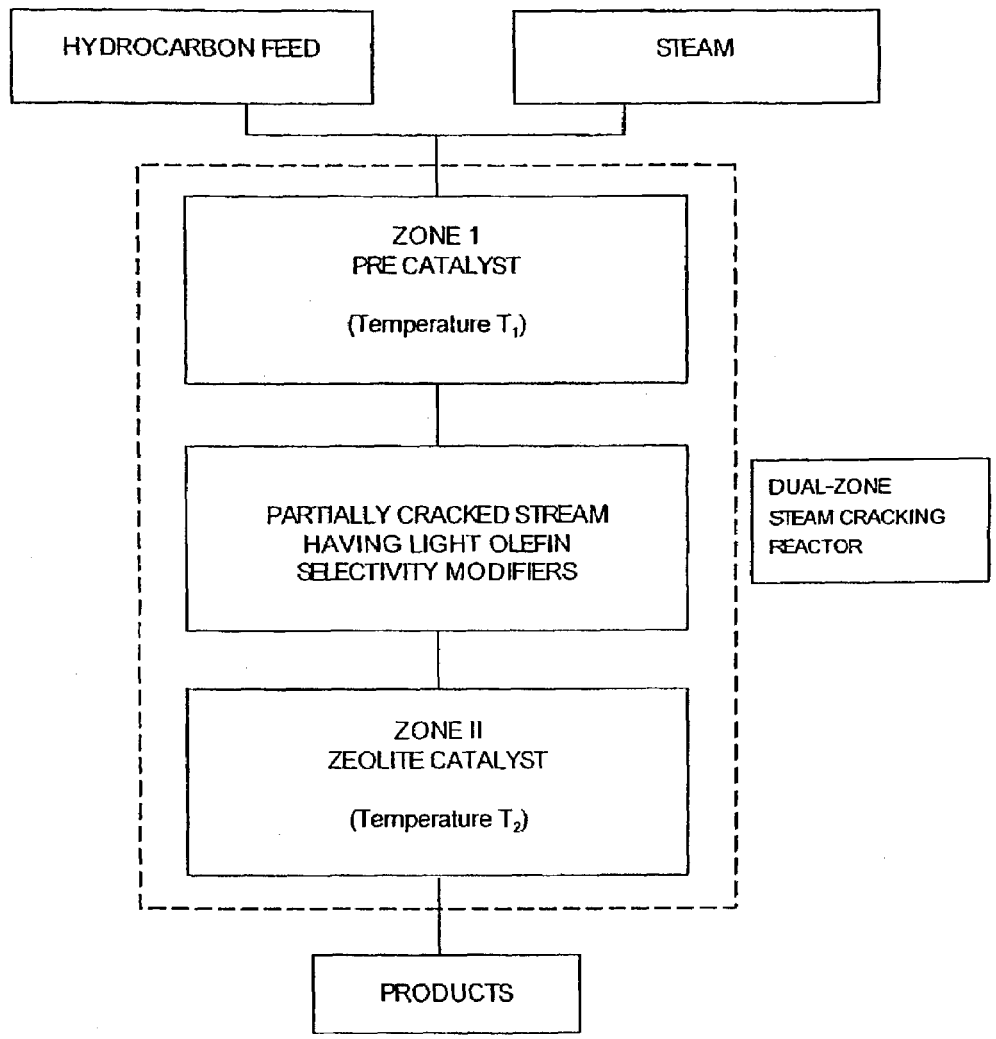

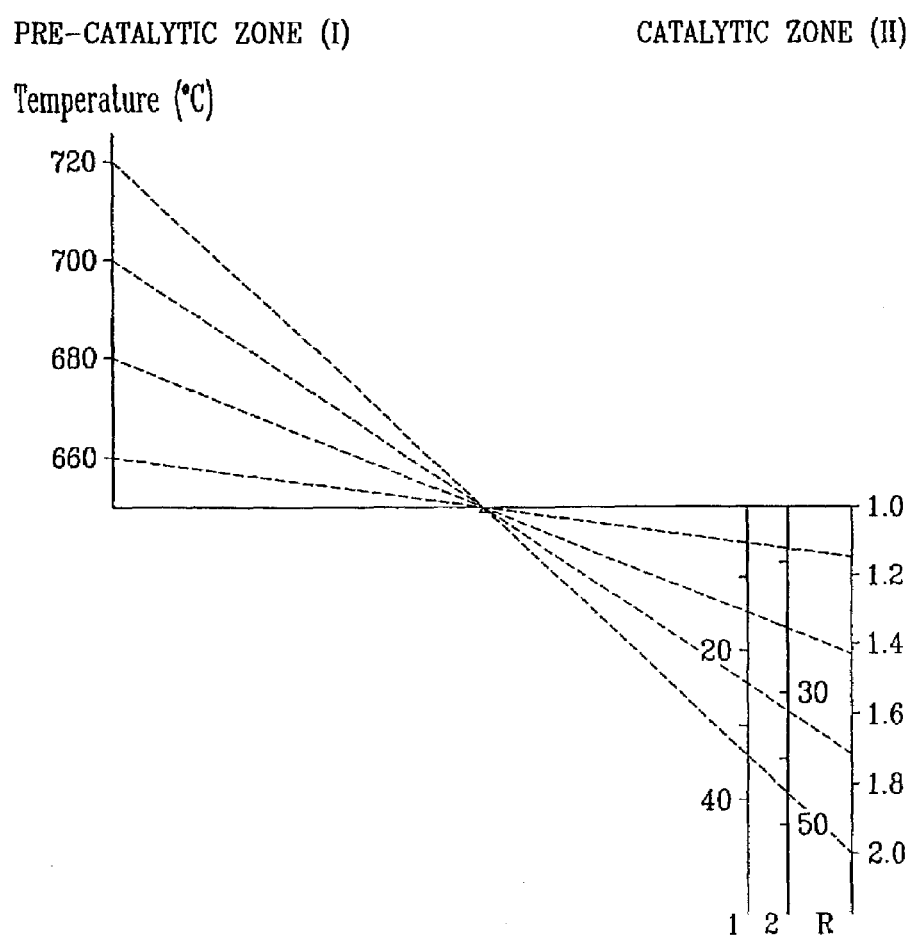

METHOD AND APPARATUS FOR SELECTIVE DEEP CATALYTIC CRACKING OF HYDROCARBONS

BACKGROUND OF THE INVENTION

1. Field of the Invention

The present invention relates to a method and related apparatus for catalytic steam cracking of hydrocarbons.

2. Description of the Prior Art

Steam cracking of hydrocarbons is one of the core processes in the petrochemical industry. Current world production of stream cracking products is estimated to reach 100 million metric tons/year of ethylene and propylene.

Basically, steam cracking comprises a step in which the hydrocarbon mixture to be transformed is mixed with steam and submitted to elevated temperatures in a tubular reactor, usually in the presence of one or more catalysts. The reaction temperature usually ranges from 700 to 900° C. according to the type of feedstock treated (the longer the hydrocarbon molecular structure, the lower the required temperature for cracking) while the residence time ranges from a few seconds to a fraction of second. The different resulting products, gaseous or liquid are then collected and separated. Thus, product distribution depends on the nature of the initial hydrocarbon mixture and the reaction conditions.

During steam cracking, light paraffins (ethane, propane and butane, obtained mainly by extraction from various natural gas sources) naphthas and other heavier petroleum cuts are broken down (cracked) into mainly:

i) light olefins: primarily ethylene and propylene,
ii) secondarily, depending on the feedstock employed, a $C_4$ cut rich in butadienes and a $C_5^+$ cut with a high content of aromatics, particularly benzene,
iii) and finally hydrogen.

Since enormous quantities of hydrocarbons are steam cracked throughout the world, even small yield or product selectivity improvements may lead to substantial commercial advantages.

Common feedstocks in steam cracking operations are ethane and LPG in the U.S.A. and naphthas or gas oils in Europe. However, in recent years, the situation has changed dramatically with the U.S.A. moving towards the use of heavier hydrocarbon feedstocks.

Market demands are currently focussed on propylene and on some longer isolefins such as isobutene and isopentenes. The latter enter in the synthesis of alkyl ethers used as octane boosters for transportation fuels. However, currently available steam cracking technology is not sufficiently flexible to respond to these or other market trends.

More than ten years ago, the present inventor had developed a method for upgrading the products of propane steam cracking, see U.S. Pat. No. 4,732,881. This process comprised adding a small catalytic reactor to a conventional propane steam cracker. The catalysts used were based on hybrid zeolite catalysts, namely ZSM5 zeolite modified with Al and Cr. Significant increases in the yield of ethylene and aromatics were obtained.

However, the prior art has so far partially failed to develop a method providing simultaneously:

(a) enhanced production of commercially valuable products light olefins (ethylene and propylene) and aromatics, and (b) higher production flexibility and selectivity for olefins, i.e. a wider range of variation for the ethylene/propylene ratio.

It is therefore an object of the present invention to provide a novel method meeting these requirements.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

SUMMARY OF THE INVENTION

In general terms, the present invention provides a method and apparatus for selective deep catalytic cracking of petroleum naphthas or other hydrocarbon feedstocks. Thus, the invention provides an apparatus for catalytic steam cracking of hydrocarbons comprising a reactor having first and second main reaction zones. The first reaction zone being heated to a first temperature between 500 to 900° C., preferably between 660 and 720° C., comprises a low-surface area, porous and thermally resistant catalytic material. The second reaction zone being heated to a second temperature, being the same or different from the first temperature and also being between 500 to 900° C., preferably between 660 and 720° C., comprises a zeolite-based catalyst. Also provided is a method for selective steam cracking of hydrocarbons comprising the steps of:

a) feeding steam and the hydrocarbons to a first zone of a steam cracking reactor, said first zone comprising a low-surface area, porous and thermally resistant catalytic material and being maintained at a given first temperature between 500 to 900° C., preferably between 660 and 720° C., to obtain a partially cracked hydrocarbon output stream comprising selectivity modifiers capable of modifying the steam cracking reactions occurring downstream from said first zone;

b) directing the output stream from said first zone to a second zone of said steam cracking reactor, said second zone being heated to a second temperature, being the same or different from the first temperature and also being between 500 to 900° C., preferably between 660 and 720° C., comprising a zeolite-based catalyst responsive to said selectivity modifiers present in the output stream from said first zone, to obtain a cracked hydrocarbon output stream rich in light olefins; and c) recovering said hydrocarbon output stream rich in light olefins.

In operation, the feed comprising the hydrocarbons to be cracked and steam, in well-defined proportions, is first sent into a pre-catalytic zone (Zone I) of a steam cracking reactor, preferably a tubular reactor. In a preferred embodiment, Zone I, contains beads of some catalytically mildly active porous material such as quartz or quartz doped with Cr—Al, is set at a temperature $T_1$. The gas stream flows then through a catalyst bed, called Zone II, where the catalytic reaction takes place. Zone II is set at temperature $T_2$ and contains a zeolite type catalyst, preferably ZSM5 zeolite or, most preferably, a hybrid zeolite catalyst. It is shown that by moderately increasing the temperature $T_1$ of Zone I, it is possible to have an increased total conversion of n-hexane used as model molecule for petroleum naphthas and an increased yield of light olefins (and aromatics), when compared to the parent ZSM-5 zeolite catalyst. The ethylene/propylene product ratio is closely dependent of the temperature $T_1$ if all other reaction parameters are kept constant and can be widely varied (from 1.0 to 2.0 for instance) for a limited range of variation of temperature $T_1$.

BRIEF DESCRIPTION OF THE DRAWINGS

FIG. 1: Flowchart schematically illustrating the method and apparatus of the present invention;

FIG. 2: Graph showing the selectivity in light olefin output versus temperature in pre-catalytic Zone I of the steam cracking reactor apparatus used in the present invention (using n-hexane as a model hydrocarbon molecule).

DETAILED DESCRIPTION OF A PREFERRED EMBODIMENT OF THE INVENTION

Before describing the present invention in detail, it is to be understood that the invention is not limited in its application to the details of method steps and conditions described herein. The invention is capable of other embodiments and of being practised in various ways. It is also to be understood that the phraseology or terminology used herein is for the purpose of description and not limitation.

Referring now to FIG. 1, a preferred embodiment of the method of the present invention will now be described. The method uses a tubular steam cracking reaction comprising two reaction zones: a pre-catalytic zone I containing a mildly active but robust catalyst and a catalytic zone II. Zone II contains a ZSM5 zeolite based catalyst, preferably of the hybrid configuration.

Still referring to FIG. 1, the feed of hydrocarbons to be cracked and steam are introduced in well-defined proportions into Zone I, a pre-catalytic zone located at the entrance of a tubular reactor (not shown). Zone I will advantageously contain a pre-catalyst composed of beads of some robust and mildly catalytic and porous material such as quartz, or quartz doped with Cr—Al. Zone I is set at a given temperature $T_1$ preferably between 500 to 900° C. Variations of the temperature of Zone I and the textural properties and/or the surface composition of the pre-catalyst are surprisingly used to achieve: (a) an increase the overall conversion achieved by the method of the present invention, (b) an increase the propensity of the method towards the production of light olefins such as ethylene and propylene and (c) to vary the end product distribution, namely the ethylene/propylene ratio.

Exiting Zone I, the gas stream is partially cracked and surprisingly contains selectivity modifiers, i.e. compounds which will affect the end product distribution, namely the ethylene/propylene ratio. Therefore, the entire method will be more selective than that using only a catalyst bed as a reaction zone. In addition, under almost all operating conditions, the final conversion rate is increased owing to the partial conversion of the feed through Zone I.

The gas and/or liquid stream exiting from Zone I then proceeds deeper into the tubular reactor by flowing through a catalyst bed, called zone II, where the main catalytic steam cracking reaction takes place. Zone II which is set at temperature $T_2$, contains a catalyst which is based on the ZSM5 zeolite or, preferably, a hybrid zeolite catalyst. Steam cracking in the presence of a zeolite type catalyst is commonly referred to as deep cracking.

As shown in FIG. 2, it is surprising to note that by increasing the temperature $T_1$ of Zone I, it is possible to have an increased total conversion of n-hexane (used as model molecule for petroleum naphthas or heavier hydrocarbon feedstocks) and an increased yield of light olefins (and aromatics). The ethylene/propylene product ratio (wt/wt) is closely dependent of the temperature $T_1$ if all other reaction parameters are kept constant and can be widely varied from 1.0 to 2.0 (for instance) for a quite limited range of variation of temperature $T_1$.

Thus, the method of the present invention, using a pre-catalyst system Zone I and a catalyst system Zone II, each having adjustable temperatures and properties, achieves dramatically higher conversion to commercial valuable products and greater flexibility and selectivity. The method of the present invention operates as a catalytic lever (hereinafter referred to as "CatLever" configuration) in which the operating conditions in Zone I can affect at will the composition of the products exiting Zone II. Hence, with such a novel method, the cracking activity of the ZSM5 zeolite based catalysts on various petroleum feeds (the so-called deep catalytic cracking) is dramatically improved and a considerable production flexibility is obtained. The novel method can be described as selective deep catalytic cracking.

The term "ZSM5 zeolite materials" is to be understood to encompass any such materials known to those skilled in the art. Without restricting the foregoing, are envisaged any zeolite catalyst materials selected from the group of: microporous aluminosilicates, microporous silicoaluminophosphates and microporous aluminophosphates having the zeolite structure, and also mesoporous silica-containing materials. Also envisaged are desilicated and desilicated/silica-reinserted zeolite materials as described in R. Le Van Mao, S. T. Le, D. Ohayon, F. Caillibot, L. Gelebart and G. Denes, Zeolites 19 (4) (1997), 270–278 and R. Le Van Mao and D. Ohayon, Proceedings 12th International Zeolite Conference, Baltimore

EXAMPLE

An example of the method of the present invention will now be described in relation to the catalytic steam cracking of n-hexane (used as a model molecule for petroleum naphthas). Although the present invention has been experimentally demonstrated based on n-hexane, this is an excellent model molecule for predicting the behaviour of other hydrocarbons, in particular longer chain hydrocarbons and their mixtures such as the ones found in petroleum naphthas, since the catalytic behaviors of these feeds are analogous.

N-hexane when sent together with some steam through Zone I, undergoes partial steam-cracking and dehydrogenation. The products of this conversion include olefins and diolefins which are known to increase—by hydrogen transfer or olefin dissociation—the selectivity towards light olefins during the reaction over zeolite based catalysts.

The probable light olefin selectivity modifiers generated in Zone I and affecting the activity and selectivity of the zeolite catalysts of Zone II are presently identified as such:

Cracking: large paraffin molecules→to small paraffin molecules+$H_2$

Aromatization: olefins, diolefins and naphtene→aromatics+$nH_2$

Hydrogen transfer: naphtene+olefins→aromatics+paraffins diolefins+paraffins→olefins+olefins Olefin dissociation: large olefins$\leftrightarrow$2 small olefins+$H_2$ Zone I contains a pre-catalyst porous material, preferably quartz having large pores and low surface area to avoid excessive coking. The surface of the porous material is used to enhance the contact effect and the pore system is used to lengthen the diffusion path of the feed in order to increase the steam-cracking conversion, thus, allowing the reaction in Zone I to be carried out at relatively low temperatures.

It is worth noting than Zone I is different from the feed preheating zone which is used in the prior art in many chemical or catalytic processes. Indeed, i) the role of Zone I is well-defined: to produce some selectivity modifiers and to help increase the final total conversion obtained at the outlet of the catalytic reactor (Zone II), and ii) the temperature of Zone I is normally (but not always) higher (at least in the case of the present invention) than the temperature of the catalyst bed.

Zone II contains a ZSM5 zeolite based catalyst or, preferably, a hybrid zeolite catalyst. The latter has been prepared by combining the ZSM5 zeolite with a Cr—Al containing cocatalyst in accordance with the method of formation of a pore continuum as described in U.S. Pat. No. 4,732,881.

The beneficial effects of the method based on two zones of conversion (with the parent ZSM5 zeolite packed in Zone II) when compared to the conventional one-zone catalytic reaction (parent ZSM5 zeolite) are as follows:
i) generally higher total conversion and always higher selectivity to light olefins (and aromatics) as evidenced by the yield increases in light olefins and light olefins+aromatics of 24% and 29%, respectively;
ii) a wide variation of the ethylene/propylene product ratio, depending on the temperature T1 of Zone I.

In particular, with the more active (Cr—Al) hybrid catalyst (tested with the two zone conversion set up) when compared to the parent ZSM5 zeolite alone (tested in a conventional tubular reactor), the yield increases in light olefins and light olefins+aromatics reach the values of 35% and 41%, respectively. This is shown in FIG. 2. In addition, the ethylene/propylene product ratio varies from 1.0 (equal to the value for the parent ZSM5 zeolite, obtained using the conventional reactor) to 2.0. This is also shown in FIG. 2.

In the following, are described in detail:
i) the preparation of the porous precatalyst (Zone I) and of the zeolite catalysts (Zone II);
ii) the experimental set-up;
iii) the testing procedure, and
iv) the catalytic conversion results along with discussion.

Preparation of the Porous Contact Filler and Catalysts

Porous precatalyst packed in the mildly catalytic zone (Zone I):

Quartz (silicon oxide, fused from Aldrich, granules) was used as porous precatalyst for the conversion zone I without any further treatment. It has the following physical properties mesh size=4–16 mesh (particle size=ca. 350 microns); surface area 0.3 m2/g, porosity=all mesopores and macropores.

Parent ZSM5 zeolite catalyst (Zone II):

This catalyst (Zeocat PZ-2/50, H-form, 1/16" extrudates) was purchased from Chemie Uetikon AG (Switzerland). It contains ca. 20 wt % of an unknown binder. Prior to the catalytic testing, it was activated in air at 700° C. overnight. Its main physical properties are: surface area=389 m2/g, microporosity=177 m2/g and Si/Al=ca. 50. This reference catalyst is referred to as HZSM5.

Hybrid catalyst containing the ZSM5 zeolite and the Cr—Al cocatalyst:
i) The ZSM-5 zeolite used was the Zeocat PZ-2/50, H-form, powder, purchased from Chemie Uetikon AG (Switzerland). It was activated in air overnight at 700° C. Its main physical properties are: surface area=483 m2/g, microporosity=277 m2/g, and Si/Al=ca. 50. This material is referred to as HZ.
ii) The cocatalyst was prepared in the following way the solid material (20 g) obtained by drying the Colloidal silica Ludox AS-40 from Dupont and then activated in air at 700° overnight, was impregnated with an aqueous solution of Cr and Al obtained by dissolving 10.0 g of $Cr(NO3)_3 \cdot 9H_2O$ and 9.0 g of sodium aluminate, all from Aldrich, in 30 ml of water. After 10 min left at room temperature, the solution was slowly (and under stirring) evaporated to dryness on a hot plate. The resulting solid material was dried at 120° C. overnight and finally activated in air at 700° C. for 5 hours. This cocatalyst is referred to as Cocat.
iii) The final hybrid catalyst, referred to as Hyb. Cat., was obtained by extrusion with bentonite as follows: first, HZ and Cocat (70 wt % and 15 wt %, respectively) were carefully mixed (a hour stirring in dry conditions); then, bentonite clay used as binder (15 wt %) was added to the previous solid mixture and the all was stirred for another hour. Water was then added dropwise until a malleable paste was obtained. The resulting catalyst extrudates were dried at 120° C. overnight and finally activated in air at 700° C. for 5 hours.

Experimental Set Up

Experiments were performed within a Lindberg triple zone series tubular furnace coupled to a Lindberg type 818 temperature control unit capable of regulating, individually, the temperature of each zone. The reactor vessel consisted of a quartz tube 95 cm in length and 2 cm in diameter. As mentioned in the previous section, Zone I (reactor inlet, ca. 30 cm in length) was packed with quartz granules. Zone II (reactor outlet, ca. 30 cm in length) was packed with catalyst extrudates. The zone which is in between Zone I and Zone II, was used as cooling zone because the temperature T1 of Zone I was always set higher than the temperature T2 of the catalytic zone (Zone II).

Testing Procedure

Liquids, namely n-hexane and water, were injected into a vaporizer using two infusion pumps. In the vaporizer, nitrogen used as carrier gas, was mixed with n-hexane vapors and steam. The gaseous stream was then sent into the tubular reactor, first in Zone I and then in Zone II.

The testing conditions are as follows:
weight of catalyst=5.0 g; W.H.S.V. (weight hourly space velocity=g of reactant, i.e. n-hexane injected per hour per g of catalyst)=1.21 h–1;
water/n-hexane molar ratio=ca. 1.0;
Nitrogen flow rate=10 ml/min, duration of a run=3.5 h.

In this series of runs, the temperature $T_2$ of Zone II was kept constant at 650° C. while the temperature $T_1$ of Zone I was varied from 660° C. to 720° C.

Product liquid and gaseous fractions were collected separately using a system of condensers. The gas phase components were analysed using a Shimadzu Mini-3 FID gas chromatograph equipped with a 3 meter-long Haysep micropacked column while the liquid phase analysis was carried out using a Hewlett-Packard 8790 FID gas chromatograph equipped with a 50 m PONA capillary column.

Results

The catalytic results are herein reported as: total n-hexane conversion and product yields.

The total n-hexane conversion (mol % or wt %) is expressed as follows:

$Ct$=100×(moles of converted n-hexane/moles of n-hexane fed)

The selectivity (to product i) is expressed in C atom % (or approximately in wt %) as follows:

$Si$=100×(number of carbon atoms of product i/number of carbon atoms of converted products)

The yield in product i is expressed (in wt %) as follows:

$Yi$=1/100×$Ct$×$Si$

Steam-Cracking Conversion of N-Hexane in the Non-Catalytic Zone, i.e. Zone I (Table 1):

Runs were performed with the zone I set at various temperature T1 (660°–720° C.) which were slightly higher than the temperature T2 of the catalytic bed (650° C.). In this series of runs, the catalyst bed was empty and Zone II was not heated. The results are reported in Table 1.

The conversion was low at 660° C. but it increased quite rapidly with the increasing temperature.

TABLE 1

Steam cracking convention of n-hexane in the pro-catalytic zone at different temperatures

| Zone I $T_1(°C.)$ | Zone II | $C_t$ | $Y_{eth}$ | $Y_{Pro}$ | $Y_{but}$ | $Y_{buta}$ | $Y_{me}$ | $Y_{p2-4}$ | $Y_{liq}$ | $Y_{ole}$ | $Y_{ole+aro}$ | $Y_{hy}$ | R |
|---|---|---|---|---|---|---|---|---|---|---|---|---|---|
| 660 | — | 31.0 | 10.8 | 9.2 | 0.7 | 4.8 | 2.0 | 2.9 | 0.7 | 25.5 | 26.2 | n.a. | 1.17 |
| 680 | — | 55.0 | 20.9 | 16.3 | 1.0 | 7.0 | 3.7 | 5.4 | 0.7 | 45.2 | 45.9 | n.a. | 1.28 |
| 700 | — | 67.1 | 27.1 | 19.5 | 1.3 | 7.6 | 4.9 | 6.4 | 0.3 | 55.5 | 55.8 | n.a. | 1.39 |
| 720 | — | 84.1 | 36.3 | 19.7 | 1.1 | 7.2 | 7.1 | 11.5 | 1.1 | 64.3 | 65.4 | n.a. | 1.84 |

$C_t$ = total n-hexane conversion (wt %); eth = ethylene; pro = propylene; but = butenes and buta = butadienes; me = methane; p2–4 = $C_2$–$C_4$ paraffins; liq = liquid hydrocarbons; ole = total olefins; ole + aro = total olefins + aromatics; R = ethylene/propylene product ratio (wt/wt); hy = hydrogen; n.a. = not available The yields in light olefins increased significantly while the yield in liquid hydrocarbons remained quite low. Within the $C_4$ unsaturates, the yields in butadienes was quite high and increased with the temperature $T_1$.

Performance of the Catalysts Tested in Various Conditions (Table 2):

i) All the catalysts tested under the Catlever conditions (both Zones heated) showed a n-hexane conversion almost equal or higher than that obtained with the HZSM5 zeolite tested under conventional conditions (i.e. with the catalyst bed only, which was heated at 650° C.).

ii) It is interesting that heating Zone I at a temperature slightly higher than the temperature of the catalyst bed, increased significantly the yields in light olefins and light olefins+aromatics.

iii) Increasing the temperature T1 increased dramatically the yield in ethylene while the yield in propylene did not significantly change. As a consequence, the ethylene/propylene product ratio increased steadily. This ratio varied in a quite comparable way as the ratio reported for the conversion at Zone I alone (Table 1).

iv) The yield in butadienes of the zeolite based catalysts tested in the Catlever conditions was significantly decreased when compared with that of the pre-catalyst tested alone (Tables 1 and 2). This shows that the diolefins (butadienes) were used by the zeolite catalysts to significantly increase yields of ethylene and aromatics.

v) The Catlever configuration induced a higher production of liquid hydrocarbons which were richer in aromatics, when compared to the HZSM5 in normal conditions of testing and also to the pre-catalytic conversion alone (Table 1).

vi) The use of the hybrid catalyst increased further the yields in light olefins and in light olefins+aromatics.

Discussion

The above results as ascribed to the combined effect of the two conversion zones (the so called Catlever effect. The selectivity enhancers created in Zone I, advantageously improve the performance of the catalyst in Zone II. In particular, the decrease of butadienes seen in the product stream was due to the hydrogen transfer within the zeolite network (Table 1 versus Table 2): this is indicative of the role of these substances in the modification of the activity and selectivity of the zeolite based catalysts. In addition, the data obtained with the hybrid catalyst (Table 2) when compared to the HZSM5 (normal conditions of testing, i.e. with no precatalytic zone, see Table 2), the increases in light olefins and light olefins+aromatics, are 35% and 41%, respectively. These increases are even more important than those obtained with the HZSM5 zeolite tested in the

TABLE 2

Activity and Selectivity of the catalysts tested in various conditions

| Zone I $T_1(°C.)$ | Zone II Catalyst | $C_t$ | $Y_{eth}$ | $Y_{Pro}$ | $Y_{but}$ | $Y_{buta}$ | $Y_{me}$ | $Y_{p2-4}$ | $Y_{aro}$ | $Y_{ole}$ | $Y_{ole+aro}$ | $Y_{hy}$ | R |
|---|---|---|---|---|---|---|---|---|---|---|---|---|---|
| No | HZSM5 | 84.0 | 23.9 | 23.7 | 3.7 | 2.5 | 3.0 | 25.0 | 2.2 | 53.8 | 56.0 | n.a. | 1.01 |
| 680 | HZSM5 | 82.0 | 26.3 | 22.4 | 6.1 | 4.1 | 5.8 | 12.5 | 4.8 | 58.9 | 63.7 | n.a. | 1.17 |
| 700 | HZSM5 | 88.0 | 33.3 | 21.6 | 3.8 | 2.5 | 9.5 | 12.8 | 4.5 | 61.2 | 65.7 | n.a. | 1.54 |
| 660 | Hyb. Cat. | 80.1 | 26.4 | 24.4 | 6.2 | 4.2 | 5.6 | 9.2 | 4.1 | 61.2 | 65.3 | n.a. | 1.08 |
| 680 | Hyb. Cat. | 86.2 | 32.9 | 24.0 | 5.1 | 3.4 | 7.1 | 9.2 | 4.5 | 65.4 | 69.9 | n.a. | 1.37 |
| 700 | Hyb. Cat. | 89.1 | 37.7 | 23.3 | 2.9 | 1.9 | 9.0 | 9.8 | 4.5 | 65.8 | 70.3 | n.a. | 1.62 |
| 720 | Hyb. Cat. | 99.5 | 44.3 | 22.5 | 3.5 | 2.3 | 10.4 | 9.9 | 6.6 | 72.6 | 79.2 | n.a. | 1.97 |

$C_t$ = total n-hexane conversion (wt %); eth = ethylene; pro = propylene; but = butenes and buta = butadienes; me = methane; p2–4 = $C_2$–$C_4$ paraffins; ole = total olefins; aro = aromatic rich liquid hydrocarbons; R = ethylene/propylene product ratio (wt/wt); hy = hydrogen; n.a. = not available Catlever conditions (Table 2). This is due to the dehydrogenating effect of the cocatalyst of the hybrid catalyst, which results in the formation of another activity and selectivity modifier.

It is to be noted that the apparatus of the present invention is not limited to a tubular reactor with two reaction zones. In fact, the catalytic zone (Zone II) may have another configuration such as that of a fluidized bed.

The invention claimed is:

1. A method for selective steam cracking of hydrocarbons into light olefins comprising ethylene and propylene, said method comprising the steps of:

a) feeding steam and the hydrocarbons to a thermal cracking zone of a reactor, said thermal cracking zone comprising a low-surface area, porous and thermally resistant material and being maintained at a given first temperature between 660 and 720° C., thereby providing a partially cracked hydrocarbon output stream comprising selectivity modifiers consisting essentially of diolefins capable of modifying the cracking reactions occurring downstream firm said thermal cracking zone;

b) directing the output stream from said thermal cracking zone to a catalytic cracking zone of said reactor, said catalytic cracking zone being heated to a second temperature, being the same or lower than the first temperature and also being between 660 and 720° C., said catalytic cracking zone comprising a zeolite-based catalyst responsive to said selectivity modifiers present in the output stream from said thermal tracking zone, thereby obtaining a cracked hydrocarbon output stream rich in light olefins, wherein said olefins comprise ethylene and propylene;

c) recovering the cracked hydrocarbon output stream from said reactor.

2. The method of claim 1 wherein the temperature in said thermal cracking zone is between 680 and 720° C.

3. The method of claim 1 wherein the temperature in said thermal cracking zone is selected so as to select the yield of light olefins present in the cracked hydrocarbon output stream recovered in step c) and to select the ratio of ethylene/propylene in the cracked hydrocarbon output stream recovered in step c).

4. The method of claim 1 wherein in step a), the low-surface area, porous and thermally resistant catalytic material is virgin or doped quartz.

5. The method of claim 4 wherein said quartz is doped with Cr—Al.

6. The method of claim 1 wherein in step b), the zeolite-based catalyst is a ZSM5 zeolite-based catalyst.

7. The method of claim 6 wherein said ZSM5 zeolite-based catalyst is a hybrid catalyst containing Cr and Al.

8. The method of claim 1 wherein steps a) and b) are conducted in a tubular reactor.

9. The method of claim 1 wherein steps a) and b) are conducted in a fluidized bed reactor.

10. The method of claim 1 wherein in step a) said hydrocarbons are rich in naphthas.

* * * * *